United States Patent [19]

Onda et al.

[11] 4,091,205

[45] May 23, 1978

[54] METHOD FOR PREPARING LOW-SUBSTITUTED CELLULOSE ETHERS

[75] Inventors: Yoshiro Onda; Hiroaki Muto, both of Ogata; Hiroshi Suzuki, Joetsu, all of Japan

[73] Assignee: Shin-Etsu Chemical Co., Ltd., Japan

[21] Appl. No.: 635,286

[22] Filed: Nov. 26, 1975

[30] Foreign Application Priority Data

Nov. 28, 1974 Japan .............................. 49-138141

[51] Int. Cl.$^2$ ................... C08B 11/20; C08B 11/193; C08B 11/08; C08B 11/12; C08B 11/02; A61K 31/72

[52] U.S. Cl. ........................................ 536/85; 536/84; 536/86; 536/91; 536/95; 536/96; 536/98; 536/99; 536/100; 424/362

[58] Field of Search .................... 424/362; 536/84, 89, 536/98, 95, 96, 100, 85, 91, 99

[56] References Cited

U.S. PATENT DOCUMENTS

| | | | |
|---|---|---|---|
| 1,448,091 | 3/1923 | Seel | 536/89 |
| 1,510,735 | 10/1924 | Baybutt | 536/89 |
| 3,251,824 | 5/1966 | Battista | 424/362 |
| 3,451,998 | 6/1969 | Alexander et al. | 536/89 |
| 3,527,751 | 9/1970 | Gill | 536/89 |

OTHER PUBLICATIONS

Rodd, E. H. "Chem. of Carbon Cpds.", vol. I, Part B, Elsevier Publ. Co., N.Y. 1952, p. 1308.

*Primary Examiner*—Natalie Trousof
*Assistant Examiner*—Cary Owens
*Attorney, Agent, or Firm*—McGlew and Tuttle

[57] ABSTRACT

In the process for the preparation of low-substituted cellulose ethers comprising the successive steps of etherification of alkali cellulose, neutralization of the crude cellulose ether, washing, drying and pulverization, the neutralization step is carried out in two stages, i.e., by first employing 5 to 80% of an acid stoichiometrically required and then adding an additional amount of the acid to complete neutralization. The cellulose ethers thus prepared can readily be pulverized into fine powder having a very good flowing property and yet an excellent binding force, and work as a suitable disintegrator in tablets.

11 Claims, No Drawings

METHOD FOR PREPARING LOW-SUBSTITUTED CELLULOSE ETHERS

FIELD OF THE INVENTION

This invention relates to a method for the preparation of low-substituted cellulose ethers useful as disintegrators in tablets or, in particular, for the preparation of cellulose ethers having an excellent binding force as well as a sufficient disintegration ability.

DESCRIPTION OF THE PRIOR ART

In the prior art, various kinds of disintegrators are known. They include carboxymethylcellulose and calcium salt thereof, raw starch, formalized gelatine, alginic acid and calcium salt thereof. Those known disintegrators have poor binding force and tend to cause capping in tableting, and the tablets obtained are unsatisfactory because of a relatively great friability and an insufficient disintegration ability.

Besides the above-mentioned disintegrators, there are other cellulose ethers with low substitution disclosed in Japanese Patent Publication No. 29473/44, U.S. Pat. No. 3,852,421 and British patent specification No. 1,362,700. These cellulose ethers, however, suffer from the same defects as described above and are not satisfactory as a disintegrator of tablets.

The inventors have conducted extensive studies on cellulose ethers with low substitution and found that the qualities of cellulose ethers as disintegrators depend largely upon conditions under which the cellulose ethers are prepared.

Usually, cellulose ethers with low substitution are prepared in the steps of conversion of cellulose to alkali cellulose, etherification of the alkali cellulose, neutralization, washing, dehydration, drying and pulverization. When the neutralization step is carried out by, for example, first dispersing or dissolving the etherified product containing free alkali in hot or cold water and then adding once an acid in an amount sufficient to neutralize all alkali, the resulting cellulose ethers have a poor binding force, bringing about the occurrence of chipping or capping to tablets during tableting and subsequent processing as well as insufficient hardness to products.

Alternatively, for a further example, when the neutralization is carried out by first dispersing the etherified product containing free alkali in an organic solvent and then adding an acid in the same manner as in the previous example, the etherified product remains in fibrous form due to its insolubility in organic solvents, the fibrous form being retained throughout subsequent drying and pulverization steps. In this case, even with the use of a hammer mill as the pulverizing machine, it is very difficult to reduce the fibrous dry material into fine powder; the resulting product is a fibrous, fluffy powder with poor flowing characteristics. If such fibrous, fluffy powder is used as a disintegrator in the formulation of a tableting mixture, a difficulty is encountered in weighing in constant portions. The poor flowing property of the fibrous, fluffy cellulose ether powder may be remedied by prolonged pulverization with a ball mill, but this disadvantageously results in the deterioration of binding force.

OBJECT OF THE INVENTION

The object of the present invention is to provide an improved method for the preparation of a cellulose ether with low substitution in the form of a finely divided powder, free from the above problems and having excellent properties as a disintegrator added to a tablet.

SUMMARY OF THE INVENTION

In accordance with the method of this invention, cellulose ethers with low substitution, for example, with a molar substitution of from 0.05 to 1.0, can be prepared by a method comprising the steps of etherifying an alkali cellulose with an etherificating agent to a crude cellulose ether, dispersing and partly dissolving the crude cellulose ether in an aqueous medium containing an acid in an amount equivalent to from 5 to 80%, preferably from 7 to 70%, of the amount stoichiometrically required for the complete neutralization of all alkali, adding an additional amount sufficient to neutralize all the remaining alkali to the aqueous medium, washing the thus completely neutralized cellulose ether with water, drying the thus washed cellulose ether, and pulverizing the thus dried cellulose ether into finely divided powder.

DETAILED DESCRIPTION OF THE INVENTION

The procedure for the etherification step in accordance with this invention is conventional. That is to say, the alkali cellulose containing free alkali is converted, by use of controlled amounts of an etherificating agent, into a cellulose ether having a molar substitution of from 0.05 to 1.0. For example, raw material pulp, such as wood pulp and cotton linter, having been immersed n an aqueous sodium hydroxide solution of 10 to 50% concentration, is squeezed to form an alkali cellulose having a NaOH/cellulose ratio of from about 0.1 to 1.2 by weight, and the alkali cellulose is reacted with an etherificating agent, such as, alkyl chloride or alkylene oxide, for 2 to 8 hours under agitation in a reactor vessel kept at a temperature ranging from 20° to 90° C. The molar substitution is necessarily in the range of from 0.05 to 1.0 as defined by the number of substitution groups per anhydrous glucose residue. When the molar substitution is outside the above-mentioned range, the resultant cellulose ether is not suitable as a disintegrator to be added to a tablet.

Next, with respect to the neutralization step in accordance with this invention, it is carried out in two stages, instead of a single stage as practiced in the prior technique, using an inorganic or organic acid.

In the first neutralization stage according to the invention, the crude cellulose ether containing free alkali and the alkali combined to the cellulose in the form of alkali cellulose is dispersed and partly dissolved in an aqueous medium containing an acid in an amount equivalent to from 5 to 80%, preferably from 7 to 70%, of the amount stoichiometrically required for the complete neutralization of all alkali. In this case, the aqueous medium in which the crude cellulose ether has been dispersed is alkaline so that the cellulose ether having a molar substitution ranging from 0.05 to 1.0 becomes partly dissolved. This partial dissolution of the cellulose ether plays a very important role for the achievement of the object of the present invention. When the amount of the acid used in the first stage of neutralization is outside the above-mentioned range, the amount of the portion of the cellulose ether dissolved is too much or too small, and the resulting final powdery product of the cellulose ether will have a poor flowability or a low binding force. In the second stage of neutralization, the same or different acid is further added to the partly neutralized mixture in order to neutralize the alkali remaining in situ after the first stage neutralization. The mixture is no more alkaline so tht the cellulose ether dissolved in the first stage neutralization becomes to reprecipitate. The partial dissolution and reprecipitation of the cellulose ether by the above-described two-stage neutralization are considered to give the desired cellulose ether product in the form of fine powder having excellent flow behavior and binding force and capable of imparting a satifactory disintegration ability to a tablet through a subsequent pulverization step, using a hammer mill alone. Optimum conditions under which the two-stage neutralization should be carried out, including the amount of the aqueous medium, the temperature of the crude cellulose ether dispersion, may be determined depending on the kinds of the cellulose ethers to be obtained.

The subsequent treatments of washing, dehydration, drying and pulverization following the neutralization step are conducted according to any conventional manners.

The mechanism by which cellulose ether products having superior quality are prepared in accordance with the present invention is presumably that the crude cellulose ether is divided, by virtue of the two-stage neutralization, in two portions, i.e., a portion of fibrous form dispersed in the aqueous medium and the other portion dissolved and reprecipitated in the same aqueous medium, and the high binding force owned by the former portion and the good pulverizability and flowability owned by the latter portion work together to produce the objective cellulose ethers having those advantageous physical properties.

The low-substituted cellulose ethers prepared by the method of this invention for use as suitable disintegrators to be added to tablets include methylcellulose, ethylcellulose, hydroxyethylcellulose, hydroxypropylcellulose, hydroxybutylcellulose, hydroxyethylmethylcellulose, hydroxyethylethylcellulose, hydroxypropylmethylcellulose, hydroxypropylethylcellulose, hydroxybutylmethylcellulose, hydroxybutylethylcellulose, carboxymethylcellulose, and salts thereof.

Following are several examples to illustrate the method of the present invention. In the examples, parts and % are all based on weight. The chemical composition and properties of the individual low-substituted cellulose ethers produced, i.e., value of the molar substitution, particle size distribution, powder characteristics including repose angle, loose bulk density and tapped bulk density, hardness, number of cappings, disintegrability and variation in weight of tablets prepared with each low-substituted cellulose ether are determined as follows.

VALUE OF THE MOLAR SUBSTITUTION

The content of the alkoxy groups was determined by the iodometry of the iodine formed from the alkyl iodide liberated by the reaction of the alkoxy groups with hydroiodic acid. The content of the hydroxyalkoxy groups was determined as the product ot the oxidative decomposition of the hydroxyalkoxy groups with chromic acid in hot.

PARTICLE SIZE DISTRIBUTION

Fractionation of 100 g of the sample was conducted with a set of Tyler Standard sieves by shaking for 20 minutes in a rotating and tapping testing sieve shaker. The distribution was expressed by the weights of the individual fractions.

POWDER CHARACTERISTICS

The repose angle, loose bulk density and tapped bulk density were determined by use of Powder Tester manufactured by Hosokawa Iron Works Co., Japan.

HARDNESS OF A TABLET

An Erweka hardness tester for tablets was employed.

NUMBER OF CAPPINGS

A friabilator with a rotating drum of 27 cm inner diameter was driven to 500 revolutions taking 20 minutes with 20 tablets to be tested contained therein, and the number of chipped or capped tablets was recorded as the number of cappings.

DISINTEGRATION TIME

Disintegration time was recorded in seconds in accordance with the testing method for tablet disintegration set forth in the Japan Pharmacopoeia, 8th Revision with water at 37 ± 2° C.

VARIATION COEFFICIENT

This was calculated from the average weight of 20 tablets and standard deviation in the weight of the tablets, and expressed in %.

EXAMPLE 1

Wood pulp was dipped in a 49% aqueous solution of sodium hydroxide and thereafter squeezed by compression to form an alkali cellulose composed of NaOH 24.1%, $Na_2CO_3$ 1.7%, cellulose 42.9% and $H_2O$ 31.8%. Into a reaction vessel were placed 100 parts of the alkali cellulose, and the vessel was filled with nitrogen gas, followed by charge of 10.5 parts of propylene oxide, and then etherification reaction was conducted under agitation with stepwise elevation of temperatures beginning with 40° C for 1 hour, then 50° C for 1 hour and finally 70° C for 1 hour, to produce 110 parts of a crude hydroxypropylcellulose. This product was subjected to neutralization in three different ways as described below.

NEUTRALIZATION I

One part of the crude hydroxypropylcellulose was dispersed in 2.5 parts of hot water at 65° C in a kneader and agitated at 30° C to complete dissolution. Subsequently, a stoichiometric amount, say, 0.33 part, of glacial acetic acid was added to the solution to precipitate the cellulose ether containing no fibrous material. The thus obtained cellulose ether is referred to as "hydroxypropylcellulose No. 1" Tables I and II to follow.

NEUTRALIZATION II

Neutralization was carried out in two stages in accordance with the present invention, using an acid. The acid used in the first and second stages are called hereinafter the primary acid and the secondary acid, respectively. For the sake of the first stage neutralization, 0.13 part of glacial acetic acid as the primary acid, the amount corresponding to about 40% of the stoichiometric amount, and 2.5 parts of water heated to 65° C were mixed together in a kneader to form a solution. To the thus formed diluted acetic acid solution was added one part of the crude ether to disperse. Then, the dispersion was kept at 30° C to allow part of the crude cellulose ether to become dissolved. Thereupon, 0.20 part of glacial acetic acid as the secondary acid, the amount being corresponding to about 60% of the stoichiometric amount, was added to give a fibrous product containing the portion of reprecipitated cellulose ether. The thus obtained cellulose ether is referred to as "hydroxypropylcellulose No. 2" in Tables I and II.

NEUTRALIZATION III

The procedure was the same as in Neutralization II except that the amount of the primary acid was 0.20 part corresponding to about 60% of the stoichiometric amount and the amount of the secondary acid was decreased to 0.13 part. The thus obtained cellulose ether is referred to as "hydroxypropylcellulose No. 3" in Tables I and II.

The hydroxypropylcellulose products above were each washed with water heated at 80° C, filtrated, dried and pulverized in a high-velocity hammer mill to form fine powder. Each hydroxypropylcellulose had the molar substitution value of hydroxypropoxy groups of about 0.28. The particle size distribution and powder characteristics are shown in Table I.

Table I

| Hydroxypropylcellulose: | No. 1* | No. 2 | No. 3 |
|---|---|---|---|
| Particle size distribution, % by weight: | | | |
| Coarser than 100 mesh | 0 | 0 | 0.1 |
| 100 mesh to 145 mesh | 0 | 1.8 | 7.3 |
| 145 mesh to 200 mesh | 0.5 | 8.7 | 18.7 |
| 200 mesh to 250 mesh | 21.1 | 25.8 | 25.4 |
| 250 mesh to 350 mesh | 21.7 | 34.1 | 33.5 |
| Finer than 350 mesh | 57.1 | 29.4 | 15.0 |
| Powder characteristics: | | | |
| Repose angle, degree | 44 | 46 | 49 |
| Loose bulk density, g/ml | 0.503 | 0.275 | 0.231 |
| Tapped bulk density, g/ml | 0.833 | 0.571 | 0.465 |

*Product by Control.

Next, a tableting test was conducted with each of the above hydroxypropylcellulose Nos. 1, 2 and 3 as the disintegrator, in parallel with a test where the disintegrator was excluded. The tests were performed by direct compression, using a rotary-type tablet machine Model HT-P-18, of Hata Iron Works, Japan, equipped with punches of 9 mm diameter and 10 mm curvature, operated with 45 r.p.m. and under 1-ton pressure. The formulations of the testing tablets and the properties of the thus obtained tablets are set out in Table II.

Table II

| Test No.: | T-1 | T-2 | T-3 | T-4 |
|---|---|---|---|---|
| Disintegrator used | None | Hydroxypropylcellulose No. 1* | Hydroxypropylcellulose No. 2 | Hydroxypropylcellulose No. 3 |
| Formulation of a tablet to be tested, parts: | | | | |
| CaHPO$_4$ | 100 | 80 | 80 | 80 |
| Disintegrator | 0 | 20 | 20 | 20 |
| Magnesium stearate | 0.5 | 0.5 | 0.5 | 0.5 |
| Properties of a tablet prepared: | | | | |
| Hardness, kg | 2.2 | 2.3 | 6.4 | 9.0 |
| Number of cappings | 20 | 20 | 0 | 0 |
| Average weight, mg | 355 | 352 | 354 | 349 |
| Variation coefficient, % | 0.65 | 0.64 | 0.72 | 0.71 |
| Disintegration time, sec. | >1800 | 8.7 | 14.9 | 16.6 |

*Product by Control.

EXAMPLE 2

Wood pulp was dipped in a 40% aqueous solution of sodium hydroxide and thereafter squeezed by compression to form an alkali cellulose composed of NaOH 19.9%, Na$_2$CO$_3$ 1.0%, cellulose 46.9% and H$_2$O 32.2%. Into a reaction vessel were placed 100 parts of the alkali cellulose, and the vessel was filled with nitrogen gas, followed by introduction of 15 parts of methyl chloride, and then etherification reaction was conducted under agitation with stepwise elevation of temperatures beginning with 40° C for 2 hours, then 50° C for 1 hour and finally 80° C for 1 hour to produce 113 parts of a crude etherified product. This product was subjected to neutralization in two different ways as described below.

NEUTRALIZATION IV

Three parts of the crude cellulose ether was dispersed in a mixed solvent consisting of 80 parts of methanol and 20 parts of water containing a stoichiometric amount, say, 0.20 part, of 35% hydrochloric acid within a mixing vessel, and neutralized completely. In this case, no dissolution of the cellulose ether took place. The neutralized product retained its fibrous form. The thus obtained cellulose ether is referred to as "methylcellulose No. 1" in Tables III and IV to follow.

NEUTRALIZATION V

One part of the crude cellulose ether was dispersed in 4 parts of water heated at 65° C containing 0.02 part of 35% hydrochloric acid corresponding to about 10% of the stoichiometric amount as the primary acid within a kneader. Then, the dispersion was kept at 30° C to allow part of the crude cellulose ether to become dissolved. Thereupon, 0.18 part of 35% hydrochloric acid as the secondary acid was added to give a fibrous product containing a reprecipitated portion of the cellulose ether. The thus obtained cellulose ether is referred to as "methylcellulose No. 2" in Table III and IV.

The methylcellulose products obtained above were each washed with water heated at about 80° C, filtrated, dried and pulverized by a high-velocity hammer mill to form fine powder. The particle size distributions and the powder characteristics of each methylcellulose are shown in Table III. In the table, methylcellulose No. 1a was what had been obtained by further subjecting methylcellulose No. 1 to milling in a vibration mill for 1 hour in order to improve its flowability. The molar substitution value of methoxy groups in each methylcellulose was 0.48.

Table III

| Methylcellulose: | No. 1* | No. 1a* | No. 2 |
|---|---|---|---|
| Particle size distribution, % by weight: | | | |
| Coarser than 100 mesh | 1.5 | 0 | 0.2 |
| 100 mesh to 145 mesh | 44.1 | 0.1 | 9.7 |
| 145 mesh to 200 mesh | 35.3 | 9.8 | 21.0 |
| 200 mesh to 250 mesh | 10.2 | 22.1 | 37.4 |
| 250 mesh to 350 mesh | 6.7 | 27.6 | 18.1 |
| Finer than 350 mesh | 2.2 | 40.6 | 13.6 |
| Powder characteristics: | | | |
| Repose angle, degree | 55 | 48 | 50 |
| Loose bulk density, g/ml | 0.176 | 0.313 | 0.212 |
| Tapped bulk density, | | | |

Table III-continued

| Methylcellulose: | No. 1* | No. 1a* | No. 2 |
|---|---|---|---|
| g/ml | 0.379 | 0.552 | 0.444 |

*Product by Control.

Next, a tableting test was conducted with each of the above methylcellulose Nos. 1, 1a and 2 as the disintegrator. In each test (T-5, T-6 or T-7) was employed the same formulation of a tablet, comprising 100 parts of lactose, 10 parts of the disintegrator, 0.5 part of magnesium stearate and 0.5 part of talc. The manner and condition of the tableting were the same as described in Example 1. In the following Table IV are shown the properties of the tablet prepared.

Table IV

| Test No.: | T-5 | T-6 | T-7 |
|---|---|---|---|
| Disintegrator used | Methyl-cellulose No. 1* | Methyl-cellulose No. 1a* | Methyl-cellulose No. 2 |
| Properties of a tablet prepared: | | | |
| Hardness, kg | 5.2 | 2.8 | 4.9 |
| Number of cappings | 0 | 5 | 0 |
| Average weight, mg | 310 | 298 | 303 |
| Variation coefficient, % | 4.01 | 1.61 | 1.55 |
| Disintegration time, sec. | 35.7 | 18.5 | 20.7 |

*Product by Control.

EXAMPLE 3

Wood pulp was dipped in a 35% aqueous solution of sodium hydroxide and thereafter squeezed by compression to form an alkali cellulose composed of NaOH 18.5%, $Na_2CO_3$ 0.7%, cellulose 43.6% and $H_2O$ 37.2%. Into a reaction vessel were placed 100 parts of the alkali cellulose and the vessel was filled with nitrogen gas, followed by introduction of 10 parts of ethylene oxide, and then etherification reaction was conducted under agitation with stepwise elevation of temperatures beginning with 30° C for 1 hour, then 35° C for 1 hour and finally 70° C for 1 hour to produce 108 parts of a crude etherified product. This product was dispersed in 1600 parts of water heated at 80° C containing 5.5 parts of glacial acetic acid as the primary acid corresponding to about b 20% of the stoichiometric amount within a mixing vessel, and partly dissolved after 22 parts of glacial acetic acid as the secondary acid corresponding to the amount sufficient to complete neutralization was added. As a result, a fibrous product containing reprecipitated portion of the cellulose ether was obtained. The product of hydroxyethylcellulose thus prepared was washed with water heated at 80° C, filtrated, dried and pulverized by a high-velocity hammer mill to form fine powder. This hydroxyethylcellulose had a molar substitution value of hydroxyethoxy groups of 0.35 with the particle size distribution and the powder characteristics as shown in Table V.

Table V

| Particle size distribution, % by weight: | |
|---|---|
| Coarser than 100 mesh | 0.7 |
| 100 mesh to 145 mesh | 3.7 |
| 145 mesh to 200 mesh | 24.6 |
| 200 mesh to 250 mesh | 13.1 |
| 250 mesh to 350 mesh | 41.1 |
| Finer than 350 mesh | 16.8 |

Table V-continued

| Powder characteristics: | |
|---|---|
| Repose angle, degree | 49 |
| Loose bulk density, g/ml | 0.264 |
| Tapped bulk density, g/ml | 0.544 |

Next, a tableting test was conducted with the above hydroxyethylcellulose as the disintegrator, in parallel with control tests carried out using conventional disintegrators instead of the hydroxyethylcellulose. The tests were performed by the wet-granule tableting process as follows. Fifty parts of lactose, 45 parts of phenathetin and 5 parts of the disintegrator were blended with an aqueous solution containing 1.7 parts of polyvinylpyrrolidone in a super-mixer and granulated by adjusting the amount of water into granules having a particle size distribution such that about 50% passed a 42 mesh sieve but remained on an 80 mesh sieve. After drying, 100 parts of the granules were blended with 0.5 part of magnesium stearate and 0.5 part of talc, and the mixture was subjected to tableting with the same conditions as described in Example 1 except that the pressure was 1.5 tons instead of 1 ton. The properties of the table thus prepared are shown in Table VI.

Table VI

| Test No.: | T-8* | T-9* | T-10* | T-11 |
|---|---|---|---|---|
| Disintegrator used | Corn starch | Calcium salt of carboxy-methyl-cellulose | Micro-crystal-line cellulose | Hydroxy-ethyl-cellulose |
| Properties of a tablet prepared: | | | | |
| Hardness, kg | 3.2 | 3.6 | 5.2 | 6.0 |
| Number of capping | 20 | 16 | 17 | 0 |
| Average weight, mg | 304 | 306 | 305 | 302 |
| Variation coefficient, % | 0.60 | 0.59 | 0.43 | 0.64 |
| Disintegration time, sec. | >1800 | 338 | >1800 | 90 |

*Control.

What is claimed is:

1. Method for preparing a cellulose ether with a molar substitution of from 0.05 to 1.0 ether groups which comprises etherifying an alkali cellulose in the presence of an etherificating agent to form a crude cellulose ether composition, neutralizing said composition in two stages: in a first stage neutralization dispersing and partly dissolving the crude cellulose ether to form a mixture in a first stage aqueous medium containing an acid in an amount equivalent to from about 5 to about 80% of the amount stoichiometrically required for the complete neutralization of all alkali groups in said mixture, in a second stage neutralization adding an additional amount sufficient to neutralize all the remaining alkali in said mixture to the said first stage aqueous medium, washing the resultant completely neutralized cellulose ether with water, drying the thus washed cellulose ether, and pulverizing the thus dried cellulose ether into finely divided powder.

2. The method as claimed in claim 1, wherein the amount of the acid contained in the first stage aqueous medium is an amount equivalent to from about 7 to about 70% of the amount stoichiometrically required for the complete neutralization of all alkali.

3. The method as claimed in claim 1, wherein the etherificating agent is a member selected from the group consisting of an alkyl halide and an alkylene oxide.

4. The method as claimed in claim 1, wherein the cellulose ether produced is methylcellulose.

5. The method as claimed in claim 1, wherein the cellulose ether produced is hydroxyethylcellulose.

6. The method as claimed in claim 1, wherein the cellulose ether produced is hydroxypropylcellulose.

7. The method as claimed in claim 1, wherein the cellulose ether produced is a member selected from the group consisting of ethylcellulose, hydroxybutylcellulose, hydroxyethylmethylcellulose, hydroxyethylcellulose, hydroxypropylmethylcellulose, hydroxybutylethylcellulose, carboxymethylcellulose and salts thereof.

8. The method as claimed in claim 1, wherein the acid is acetic acid.

9. The method as claimed in claim 3, wherein the acid is acetic acid and the cellulose ether produced is methycellulose.

10. The method as claimed in claim 1, wherein the acid is hydrochloric acid.

11. The method as claimed in claim 1, wherein the dried cellulose ether is pulverized by a hammer mill.

* * * * *